(12) United States Patent
Watson et al.

(10) Patent No.: US 12,226,590 B2
(45) Date of Patent: Feb. 18, 2025

(54) ANNULUS PLANE CATHETER

(71) Applicant: Apparent LLC, Santa Rosa, CA (US)

(72) Inventors: James R. Watson, Santa Rosa, CA (US); Reginald Low, Sacramento, CA (US)

(73) Assignee: APPARENT, LLC, Santa Rosa, CA (US)

( * ) Notice: Subject to any disclaimer, the term of this patent is extended or adjusted under 35 U.S.C. 154(b) by 332 days.

(21) Appl. No.: 18/049,524

(22) Filed: Oct. 25, 2022

(65) Prior Publication Data

US 2023/0075075 A1    Mar. 9, 2023

Related U.S. Application Data

(62) Division of application No. 16/449,072, filed on Jun. 21, 2019, now Pat. No. 11,534,574.

(51) Int. Cl.
*A61M 25/01* (2006.01)
*A61F 2/24* (2006.01)
*A61M 25/00* (2006.01)

(52) U.S. Cl.
CPC ....... *A61M 25/0041* (2013.01); *A61F 2/2427* (2013.01); *A61M 25/003* (2013.01); *A61M 25/0108* (2013.01); *A61M 25/0136* (2013.01); *A61M 25/0147* (2013.01)

(58) Field of Classification Search
CPC ............ A61M 25/0041; A61M 25/003; A61M 25/0108; A61M 25/0136; A61M 25/0147; A61M 2025/0034; A61M 2210/125; A61M 25/0152; A61M 2025/0175; A61M 25/0026; A61M 25/0074; A61M 25/0082; A61M 25/04; A61F 2/2427; A61F 2/2439
See application file for complete search history.

(56) References Cited

U.S. PATENT DOCUMENTS 5,630,823 A * 5/1997 Schmitz-Rode ............................ A61B 17/320725
606/128
2013/0109960 A1 * 5/2013 Stinis ................ A61M 25/0082
623/2.11

* cited by examiner

*Primary Examiner* — Joel Lamprecht
(74) *Attorney, Agent, or Firm* — Andrew F. Young; NOLTE LACKENBACH SIEGEL (57) ABSTRACT

A coaxial multilumen annulus plane catheter, including an outer pigtail catheter enclosing one or two additional lumens, each housing either a slidable shaped wire or a second pigtail catheter shaped to fit into a wide range of annulus diameters and/or depths. In embodiments, the device may include a catheter delivery handle with thumb/finger-actuated sliders that extend or retract the shaped wires and are sized to enable side-to-side or radial motion, imparting a torque to the pre-shaped wires which translates the length of the wires to enable individually controlled rotation or sweep of each wire to accommodate different annulus diameters. The delivery handle includes hemostasis controls and flush ports. In other embodiments, a handle is obviated by direct lumen axial and rotational control at a proximal end.

14 Claims, 11 Drawing Sheets

ANNULUS PLANE CATHETER

CROSS REFERENCES TO RELATED APPLICATIONS

The present application is a divisional application of U.S. patent application Ser. No. 16/449,072, now U.S. patent Ser, No. 11,534,574, filed Jun. 21, 2019 (Jun. 21, 2019), which, in turn, claims the benefit of the filing date of U.S. Provisional Patent Application Ser. No. 62/688,331, filed Jun. 21, 2018 (Jun. 21, 2018), which application is incorporated in its entirety by reference herein.

STATEMENT REGARDING FEDERALLY SPONSORED RESEARCH OR DEVELOPMENT

Not applicable.

THE NAMES OR PARTIES TO A JOINT RESEARCH AGREEMENT

Not applicable.

INCORPORATION BY REFERENCE OF MATERIAL SUBMITTED ON A COMPACT DISC

Not applicable.

SEQUENCE LISTING

Not applicable.

BACKGROUND OF THE INVENTION

Field of the Invention: The present invention relates most generally to medical devices, and more particularly a catheter delivery system, and still more particularly a catheter delivery system and method for precisely locating the cardiac valve annulus (or basal ring) for equally precise placement of a prosthetic aortic valve.

Background Discussion: Among the many causes of heart failure, a leading cause is heart valve failure or malfunction. Valve malfunction, and resulting valve regurgitation, can be caused by (among other things) congenital heart valve disease, endocarditis, rheumatic fever, Marfan syndrome or other diseases leading to enlargement of the aortic valve, damage to the aorta proximate the valve, and or disease associated with age (i.e., acquired aortic valve disease).

Generally, a damaged or diseased heart valve is replaced with a prosthetic valve. Historically, this was accomplished using an open surgical procedure in which the patient's heart is accessed through a thoracotomy or a sternotomy. A new valve was then secured to existing cardiac tissue using sutures. The open procedure had high morbidity rates and protracted recovery times. Further, the procedure itself is complicated, likely involving the use of a heart bypass machine.

Surgical complications, recovery times, costs, the desirability of less invasive procedures, and other factors have driven advances in transcatheter techniques for delivering valve prosthetics to involved sites. Indeed, the state of the art currently is to use an intravascular transcatheter valve replacement procedure.

Proper placement of a replacement valve using a transcatheter aortic valve replacement procedure depends on a very precise identification of the aortic annulus plane. This plane is a "virtual" plane formed by geometrically surrounding and connecting the basal attachment points (or hinge points) of the aortic valvular leaflets. Failure to properly identify the size and location of the annulus plane may result in post-surgical leaks, movement of the prosthesis, annulus rupture, or artery occlusion. The annulus identification procedure typically entails the use of a contrast media injected into the patient's circulatory system. Contrast is a radiopaque solution. It is injected via a catheter into a patient's vasculature and used in conjunction with fluoroscopy to illustrate the anatomical features of the patient. Many elderly patients or those with renal insufficiency may not be able to tolerate contrast media used during a Applicant: Apparent LLC Filing Date: Oct. 25, 2022 (Oct. 25, 2022) clinical interventional procedure, owing either to the inability of the kidneys to filter or process a large molecule, such as iodinated contrast from, the bloodstream, or due to kidney loss. Any reduction in contrast usage will typically improve patient recovery times.

A principal objective of the inventive annulus plane catheter is to eliminate the need for contrast during a transcatheter aortic valve replacement procedure. When used in an aortic valve replacement procedure, the contrast is typically injected into the vasculature, via a pigtail catheter, to obtain real-time moving images (using a fluoroscope) the three cusps of the aortic valve. A physician rotates the fluoroscopic C-arm to align the bottom of the three cusps (the hinge points or basal attachments at the nadir of each cusp) to create a plane. It is important during this procedure to visualize the relative or virtual plane created by the basal attachments at the bottom of the cusps in order to accurately position the new transcatheter aortic valve. If the replacement valve is placed too high in relation to the relative plane, this may obstruct one of the coronary arteries, prevent blood perfusion to the heart muscle, or allow for inadvertent migration of the prosthesis. If the replacement aortic valve is placed too low, it may obstruct the mitral valve, allow blood to flow around the new valve in the diastolic phase, or reduce cardiac output. If it is too large, it may cause an annulus rupture. Determination of the size and location of the virtual annulus plane is therefore important regardless of the replacement aortic valve design, whether it is balloon-expandable or self-expandable nitinol stent system; misplacement of the aortic valve can result in patient safety and/or hemodynamic issues.

The use of the inventive annulus plane catheter in identifying the native valve annulus under fluoroscopy eliminates the need to use contrast media during this procedural step and thus increases patient safety and recovery.

The typical angiographic pigtail catheter in current use only identifies the bottom of a single valve cusp when positioned near the annulus. Using such an instrument with only a single reference point, it is impossible to define the annulus plane. The inventive annulus plane catheter defines the bottom portion of multiple valve cusps simultaneously, thus creating multiple reference points proximate the respective left, right, and NC nadirs of the cusps, with which to align the C-arm fluoroscope and to define the virtual annulus plane prior to valve deployment.

Any interventional procedure that requires the determination of a relative fluoroscopic plane within the vasculature or anatomy may benefit from the use of a variation of this device. It could also be used as a method to align insertion needles by placing one or more shaped wires at or near the position of insertion. The shaped wire(s) then become(s) the target for the needle. Spaced-apart shaped wires may be used to indicate an optimal injection path by geometrically connecting the centers of the wires and using the path of the connecting line for alignment and orientation.

BRIEF SUMMARY OF THE INVENTION

The present invention is an annulus plane catheter that defines the virtual annulus plane of the aortic valve without the use of contrast media. It can be used either before or during the TAVR procedure. In its most essential aspect, principal components include: a pigtail catheter with radiopaque markers and curvatures similar to existing straight or angled pigtail angiographic catheters, but including additional lumens; two radiopaque wires shaped to fit into a wide range of annulus diameters and/or depths that slide freely within the additional lumens; and a catheter delivery handle having thumb/finger-actuated sliders that extend or retract the shaped wires. The handle sliders may incorporate visual markers to identify each wire and to incorporate side-to-side or radial motion, thereby imparting a torque to the pre-shaped wires, which is translated down the length of the wires from the handle to the shaped distal ends, thereby enabling individually controlled rotation or sweep of each wire to accommodate different annulus diameters. The catheter delivery handle also incorporates hemostasis controls and flush ports. It may be used with or without a guidewire.

Other configurations of the annulus plane catheter include additional radiopaque wires, various actuating mechanisms in the handle, including rotational elements rather than reciprocating elements, removal of the pigtail feature, elimination of the guidewire lumen, and using only radiopaque wires. A variation of the annulus catheter concept may include multiple coaxial lumens with and/or without side ports to allow internal luminal catheters to exit the main catheter lumen and engage the annulus. The multi-coaxial lumen catheter handle may include various methods to actuate each lumen such as knobs, sliders and/or rotating rings or be composed of separate individually controlled lumens with hemostasis valves and/or flush ports. The multi-coaxial lumen catheter may also employ the use of reverse curvature pigtails to better engage the base of each individual cusp. Other variations may be included in embodiments of the invention without departing from the spirit and scope of the inventive concept.

The foregoing summary broadly sets out the more important features of the present invention so that the detailed description that follows may be better understood, and so that the present contributions to the art may be better appreciated. There are additional features of the invention that will be described in the detailed description of the preferred embodiments of the invention which will form the subject matter of the claims appended hereto.

Accordingly, before explaining the preferred embodiment of the disclosure in detail, it is to be understood that the disclosure is not limited in its application to the details of the construction and the arrangements set forth in the following description or illustrated in the drawings. The inventive apparatus described herein is capable of other embodiments and of being practiced and carried out in various ways.

Also, it is to be understood that the terminology and phraseology employed herein are for descriptive purposes only, and not limitation. Where specific dimensional and material specifications have been included or omitted from the specification or the claims, or both, it is to be understood that the same are not to be incorporated into the appended claims.

As such, those skilled in the art will appreciate that the conception, upon which this disclosure is based may readily be used as a basis for designing other structures, methods, and systems for carrying out the several purposes of the present invention. It is important, therefore, that the claims are regarded as including such equivalent constructions as far as they do not depart from the spirit and scope of the present invention. Rather, the fundamental aspects of the invention, along with the various features and structures that characterize the invention, are pointed out with particularity in the claims annexed to and forming a part of this disclosure. For a better understanding of the present invention, its advantages and the specific objects attained by its uses, reference should be made to the accompanying drawings and descriptive matter in which there are illustrated the preferred embodiment.

BRIEF DESCRIPTION OF SEVERAL VIEWS OF THE DRAWINGS

The invention will be better understood and objects other than those set forth above will become apparent when consideration is given to the following detailed description thereof. Such description makes reference to the annexed drawings wherein.

DETAILED DESCRIPTION OF THE INVENTION

Referring generally to FIGS. 1 through 23, wherein like reference numerals refer to like components in the various views, there is illustrated therein an inventive catheter delivery system for transcatheter aortic valve replacement surgery. In a preferred embodiment, FIGS. 1-19, generally denominated 40 herein, wherein the views feature an embodiment of the inventive annulus plane catheter.

As seen in FIGS. 1-19, components comprising an embodiment of the inventive catheter include: a pigtail catheter with radiopaque markers and curvatures similar to existing pigtail angiographic catheters but with either: (1) additional lumens, two radiopaque wires shaped to fit into a wide range of annulus diameters and/or depths that slide freely within the extra lumens, and a catheter delivery handle having thumb/finger actuated sliders that extend or retract the shaped wires, wherein the handle sliders may incorporate visual markers to identify each wire and to incorporate side-to-side motion enabling individually controlled rotation of each wire to accommodate different annulus diameters; or (2) coaxial lumens; two pigtail catheters shaped to fit into a wide range of annulus diameters and/or depths that slide freely over the central pre-shaped guidewire, and a catheter delivery handle having thumb/finger actuated sliders that extend or retract the coaxial pigtail catheters. The handle sliders may incorporate visual markers to identify each pigtail catheter and to incorporate side-to-side motion enabling individually controlled rotation of each pigtail catheter to accommodate different annulus diameters. The catheter delivery handle also incorporates hemostasis controls, flush ports, and may or may not be used with a guidewire.

Thus, and referring now to FIGS. 1-13, it will be seen that the annulus plane catheter of the present invention 40 includes a handle 42 operatively coupled to a multilumen catheter 44. The handle 42 has a substantially hollow interior 46 for capturing the proximal end 150 of the outer tubular member 50 of the multilumen catheter and for housing operative control components (discussed fully below). The handle is generally cylindrical but expands gently at its proximal portion 52 into an ergonomically shaped butt end 54. Extending distally and axially from the distal end 56 of the handle, the outer tubular member 50 emerges from the handle housing in a strain relief portion 58 to prevent kinking during use.

The outer tubular member extends distally to a distal end portion 60, from which a pigtail catheter 62 extends, and where pre-shaped wires 64, 66 extend from and retract into distal wire ports 68, 70, respectively. Distal (end) portions of the pigtail catheter may include side ports to promote contrast injection distribution, and the pre-shaped wires each have radiopaque markers, not shown but well understood in the art (radiopaque polymer materials may be employed instead of radiopaque coatings). The pre-shaped wires may be sufficiently dense to be easily seen using fluoroscopy and thus to eliminate the need for additional radiopaque coatings or materials.

The handle includes first and second (respectively, upper and lower) halves 72, 74, joined at their respective perimeter edges 76, 78, and secured together with assembly screws 80. The handle has a proximal end 82 and a distal end 84. Interior handle structure includes a medial boss 86 positioned at or near the center of the handle interior and a distal boss 88 at the distal end. The medial boss partitions the housing interior into a proximal half 46a and a distal half 46b. Recesses 86a, 86b, 86c, of the medial boss 86 of the upper half of the housing, and complementary recesses in the housing lower half (not shown), as well as recesses 88a, 88b, 88c in the housing upper half of the distal boss 88, and the complementary recesses (not shown) in the housing lower half, provide spaces and surfaces for capturing the ends of slider rods 90, 92. Control sliders 94, 96, are slidably disposed on the control rods. The bosses also capture and center the outer tubular member 50 of the multilumen catheter 44.

The slider controls each include a sleeve 98, 100 slidingly disposed around the slider rods and thus disposed interiorly in the housing, external buttons 102, 104, and planar blades 106, 108 joining the sleeves and the external buttons. The external buttons preferably include surface features 110, 112, such as knurling or ridges, to enhance slip-free finger engagement, and they include curvature generally matching the curvature along the exterior side 114 of the first half 72 of the housing.

Each slider control sleeve includes a hole 98a, 100a, into which the proximal end 64a, 66a, of one of the pre-shaped wires is inserted and affixed. The slider controls move proximally and distally (i.e., longitudinally) in parallel longitudinal slots 116, 118, cut in the upper housing half 72 to move the distal ends 64, 66 into and out from the ports 68, 70. The slots are sized to allow arcuate (radial) motion of the slider controls of approximately 10-25 degrees. In this manner, the user may impart a torque to the proximal ends of the pre-shaped wires. The wires are fabricated from materials that will translate the torque the entire length of the wire, such that torque control inputs result in a rotational (sweeping) motion of the loop portions of the wires. This may be employed to explore the valve cusps to precisely locate each cusp nadir and in so doing the annulus plane.

Figure 1:
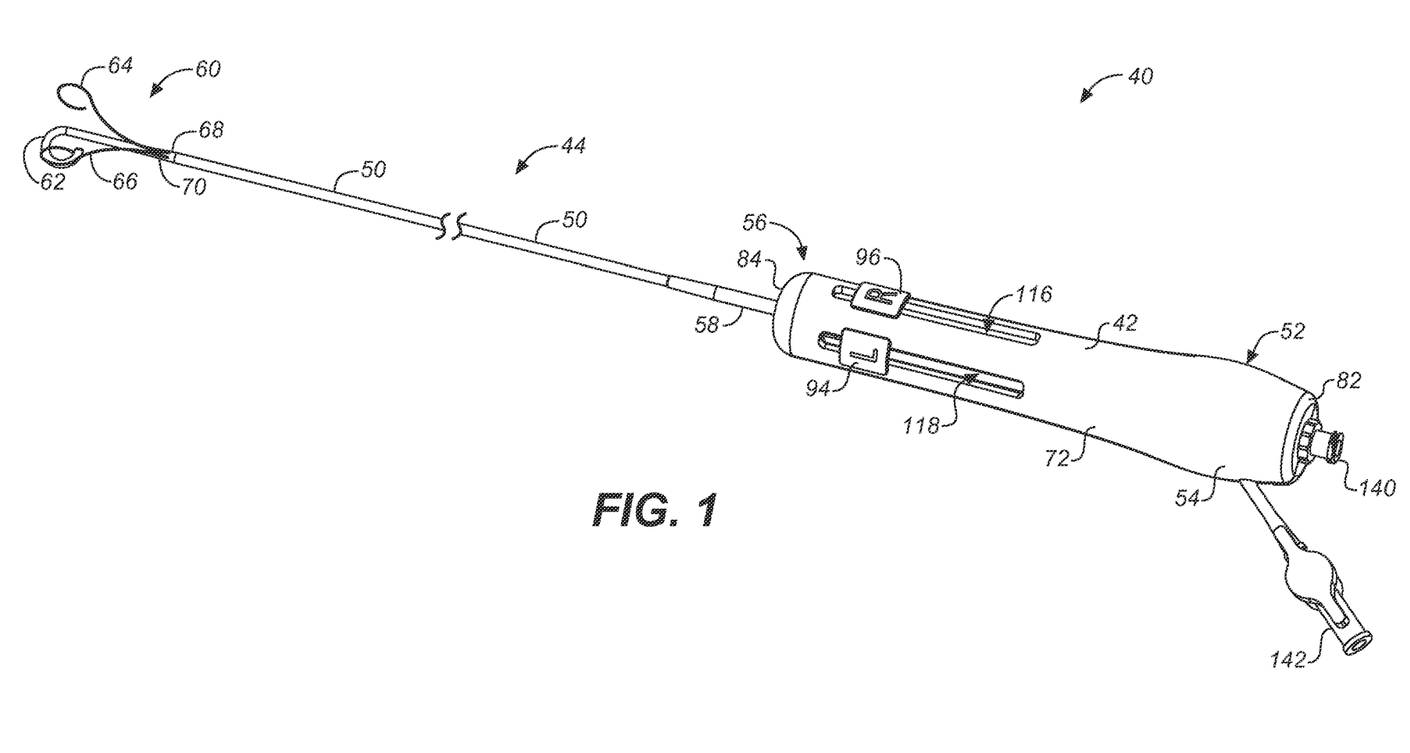
FIG. 1 is an upper left side proximal end perspective view of the assembled annulus plane catheter of the present invention.
Figure 2:
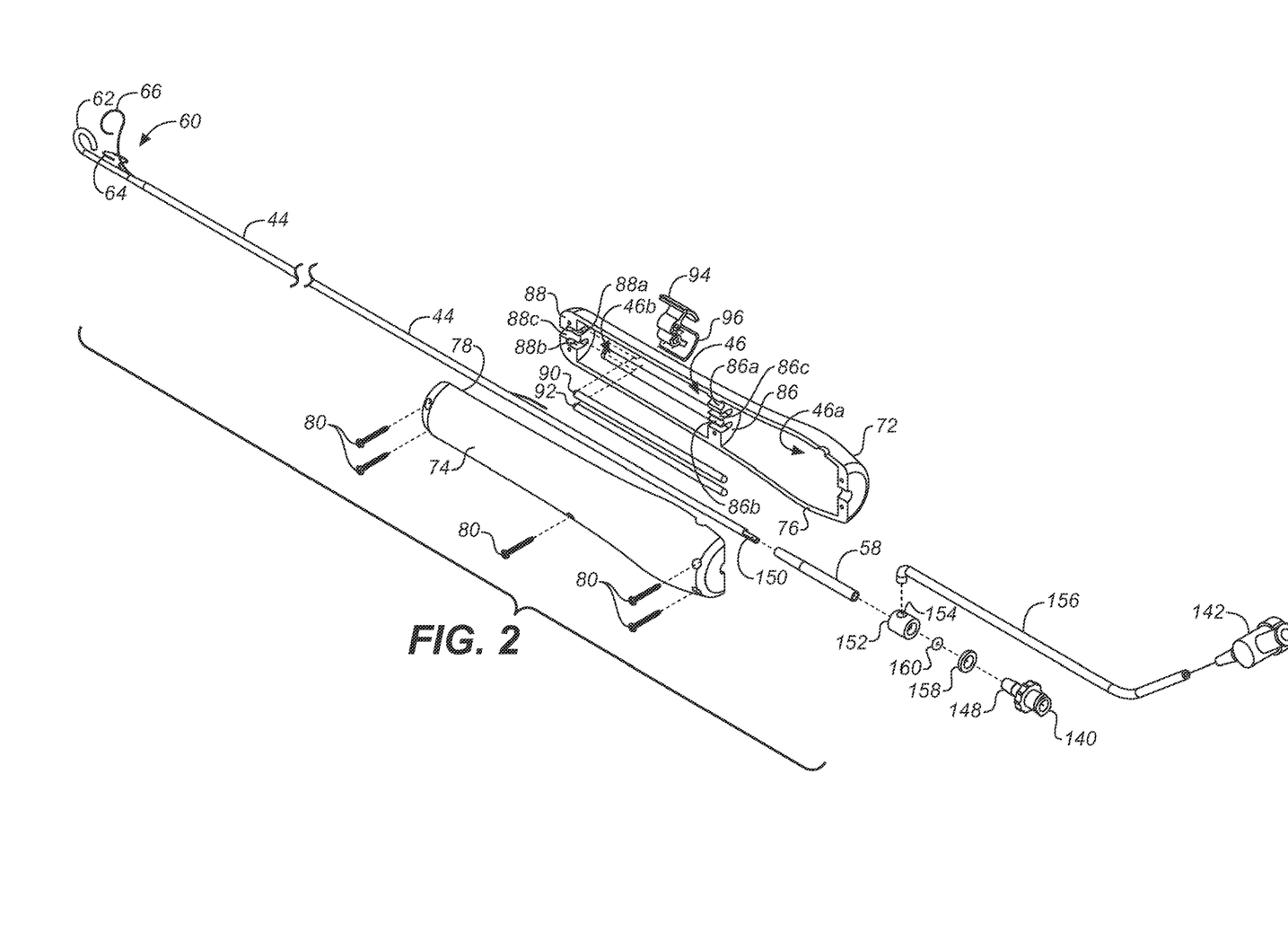
FIG. 2 is an exploded view thereof, this view seen rotated 90 degrees CW in relation to the view of FIG. 1, as viewed from the handle end.
Figure 3:
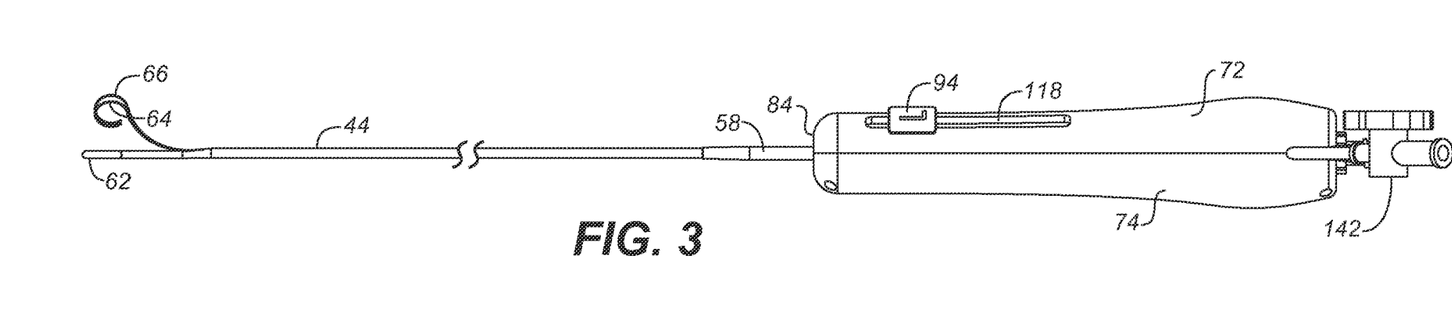
FIG. 3 is a left side view in elevation thereof.
Figure 4:
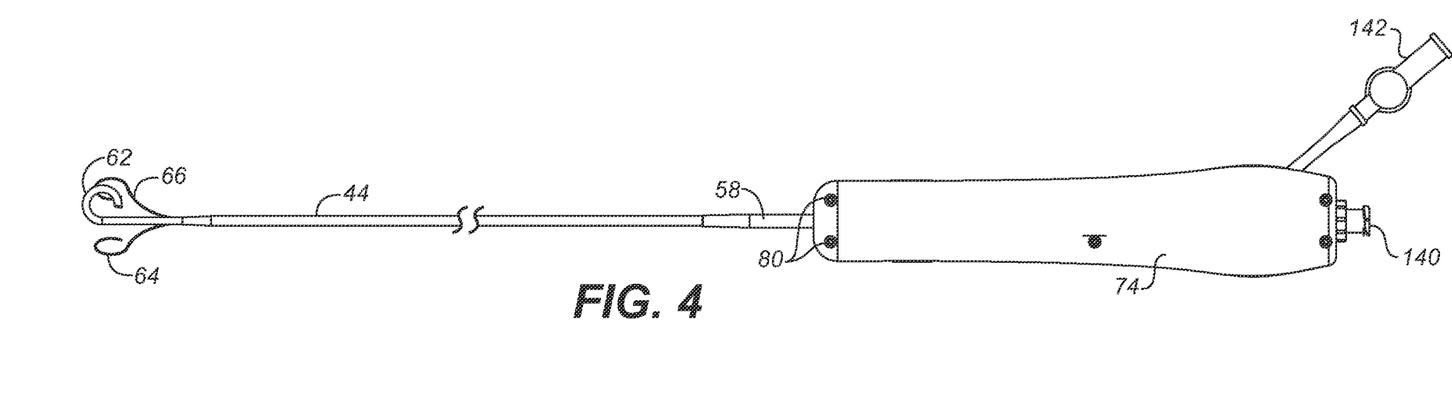
FIG. 4 is a bottom plan view thereof.
Figure 5:
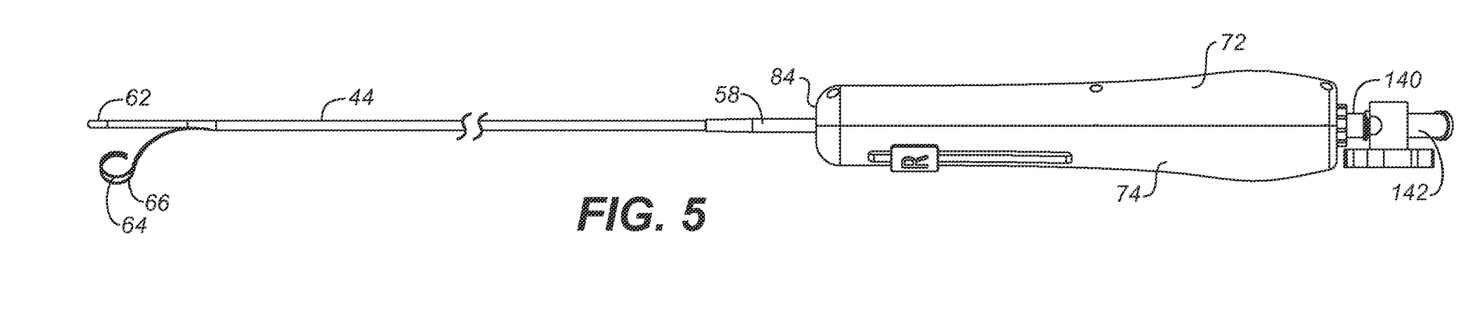
FIG. 5 is a right side view in elevation thereof, showing the pre-shaped wire controls in an inverted orientation.
Figures 6, 7, 8:
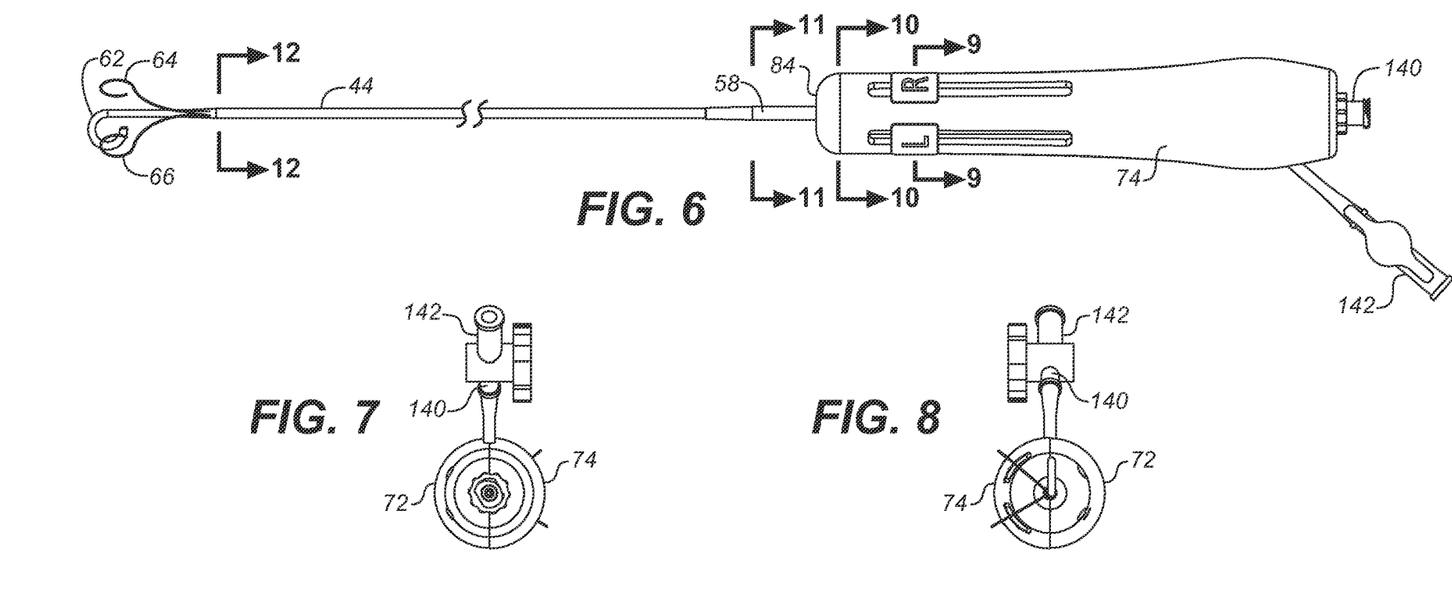
FIG. 6 is a top plan view thereof.
FIG. 7 is a proximal end view in elevation thereof.
FIG. 8 is a distal end view in elevation thereof.
Figure 9:
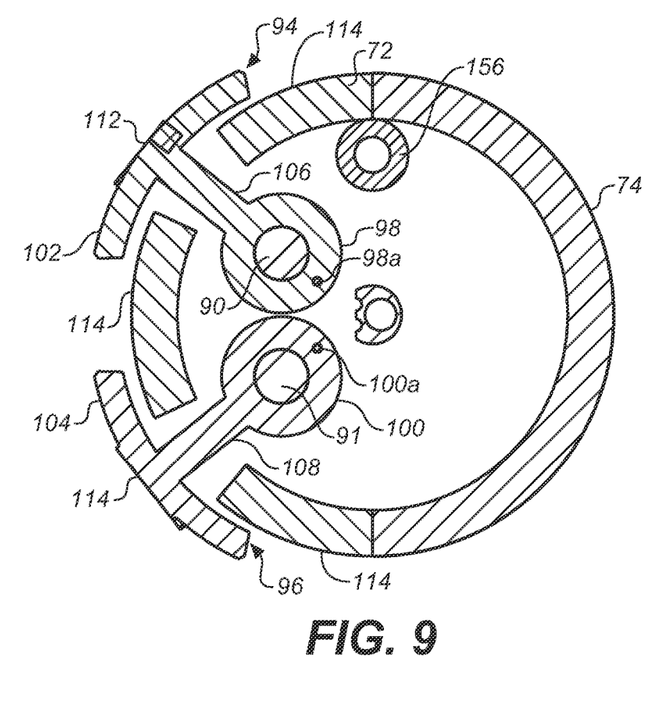
FIG. 9 is a cross-sectional distal end view showing the cut plane as taken along section line 9-9 of FIG. 6.
Figure 10:
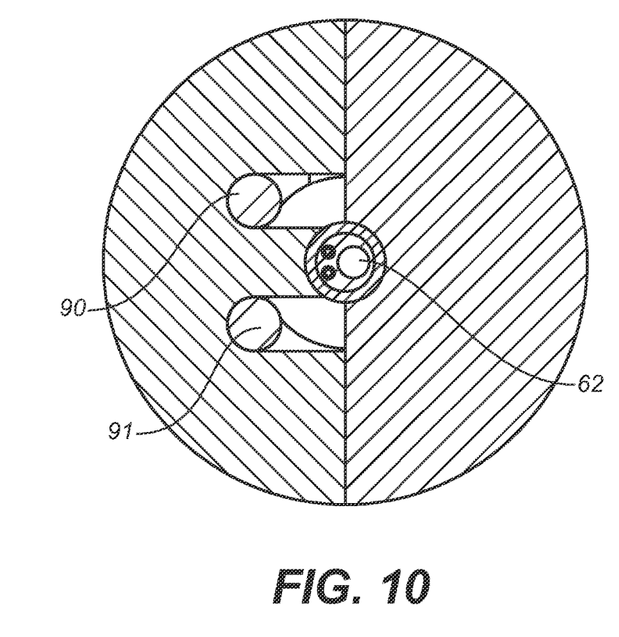
FIG. 10 is the same view taken along section line 10-10 of FIG. 6.
Figure 11:
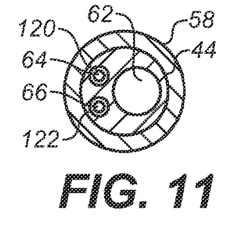
FIG. 11 is the same view taken along section line 11-11 of FIG. 6.
Figure 12:
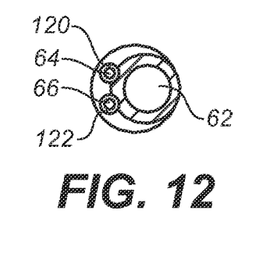
FIG. 12 is the same view taken along section line 12-12 of FIG. 6.

Looking now at the cross-sectional views of FIGS. 11-12, the multilumen catheter 44 is enclosed by strain relief 58, which feeds immediately distally from the handle housing 72 and 74. Both the strain relief 58 and multilumen catheter 44 enclose the pre-shaped wire lumens 120, 122 through which pre-shaped wires 64, 66 are slidingly disposed.

Figure 13:
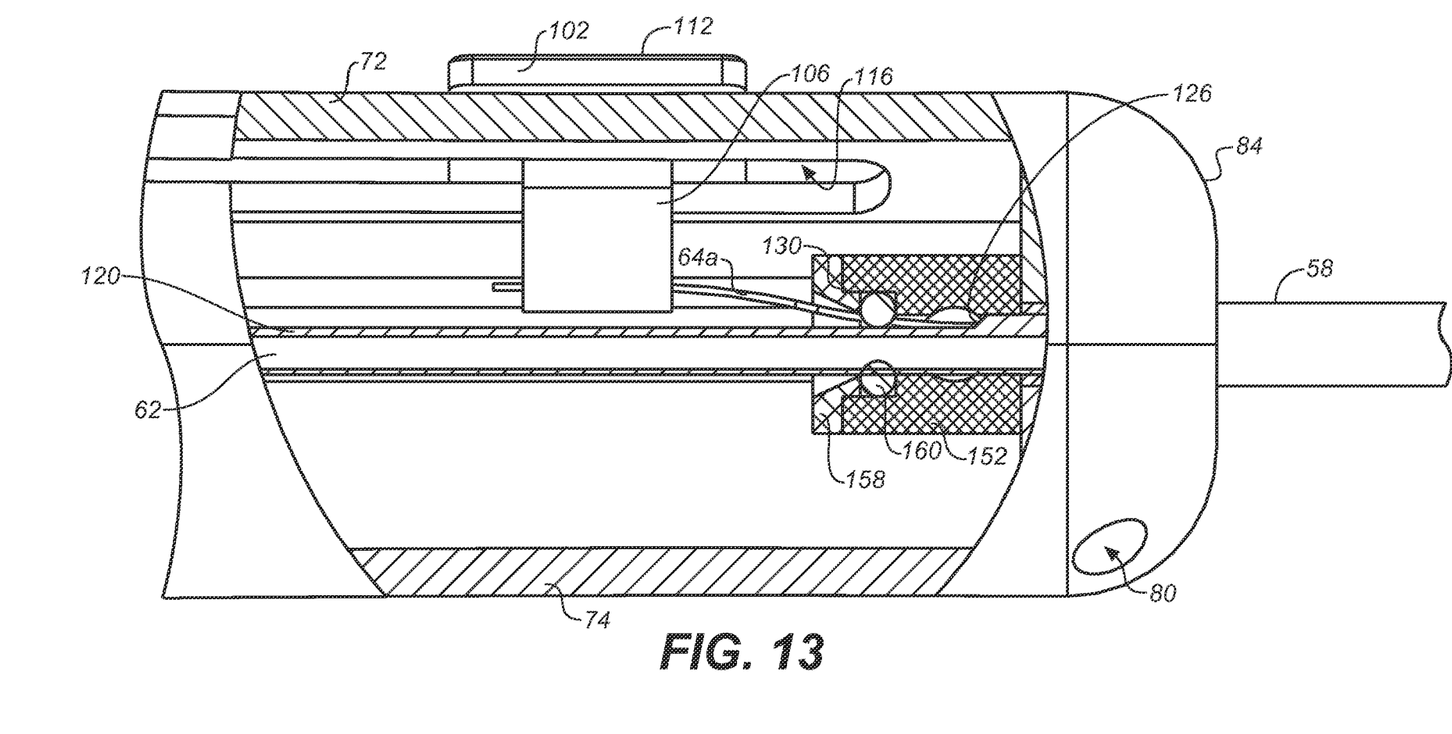
FIG. 13 is a partial cutaway and cross-sectional view showing a portion of the handle and details of the slider shaped wire linkages.

Looking next at FIG. 13, there is shown detail of how the sliders are structurally and operatively connected to the proximal end 64a (only one wire shown in the view) of the pre-shaped wires. As can be seen, each pre-shaped wire feeds through a fitting 152 into a wire lumen 120 at a proximal wire insertion port 126, and slides under O-ring 160 disposed in a channel 130 and secured by a cap or keeper 158, which provide a fluid seal for the wire lumen.

Figure 14:
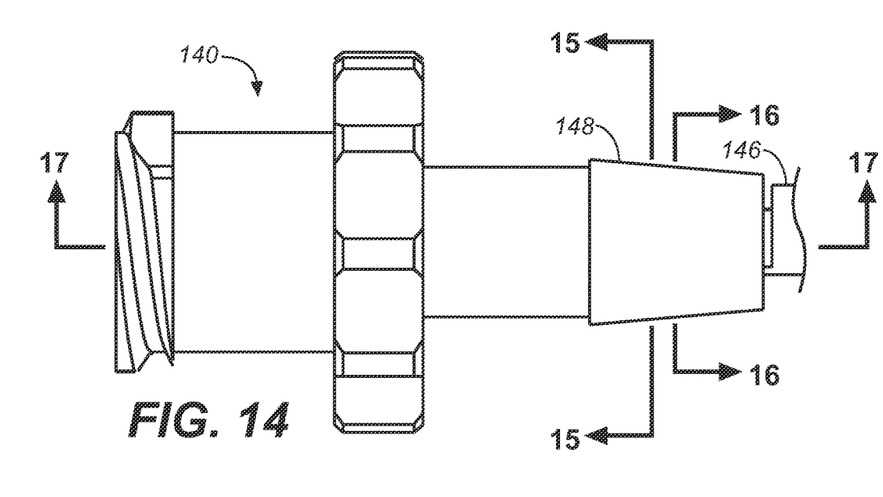
FIG. 14 is a side view in elevation of the guidewire flush port disposed on the proximal end of the catheter handle (the handle body not shown in this view)
Figure 15:
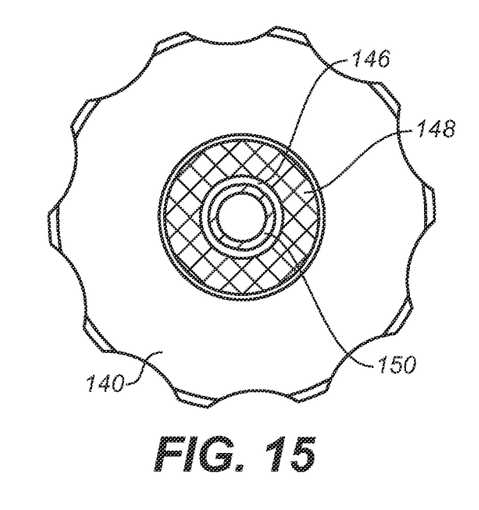
FIG. 15 is a cross-sectional distal end view in elevation of the flush port of FIG. 14 taken section line 15-15 (handle body not shown)
Figure 16:
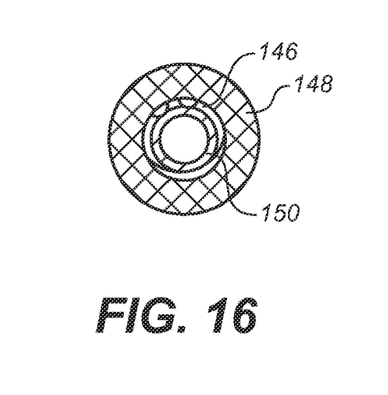
FIG. 16 is a cross-sectional proximal end view in elevation taken along section line 16-16 of FIG. 14.
Figure 17:
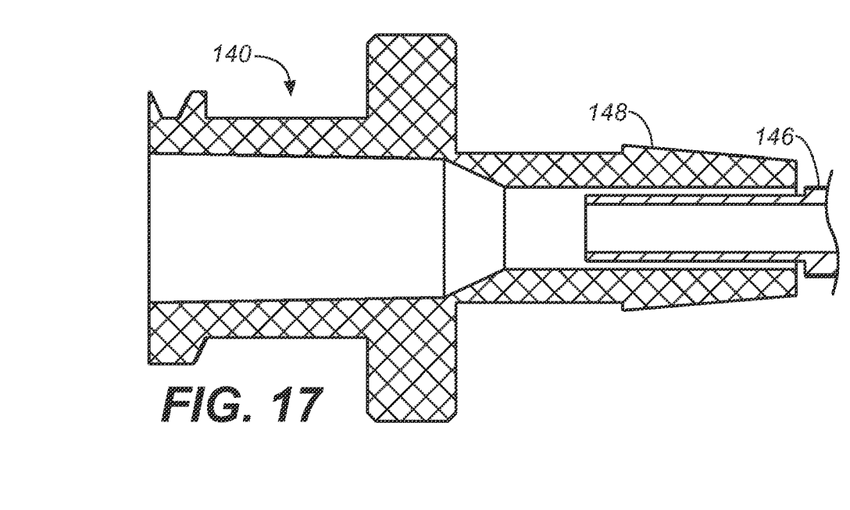
FIG. 17 is a cross-sectional side view in elevation taken along section line 17-17 of FIG. 14.

Disposed within the proximal half 46a of the housing interior are components connecting the multilumen catheter with first and second flush ports 140, 142 to provide fluid paths for introducing solutions to prevent catheter occlusion and clot formation. The proximal end 150 of the multilumen catheter 44 fits through the female T-fitting 152, which includes an inlet 154 into which a feed tube 156 is inserted and is in fluid communication with the second flush port 142. Scaling of the first flush port and T-fitting 152 is accomplished by bonding the distal edge to the multi-lumen and proximally with an O-ring 160 and affixed keeper or cap 158. The flush port 140 components include the proximal end 150 bonded to the female end 148 of the flush port 140.

Figure 18:
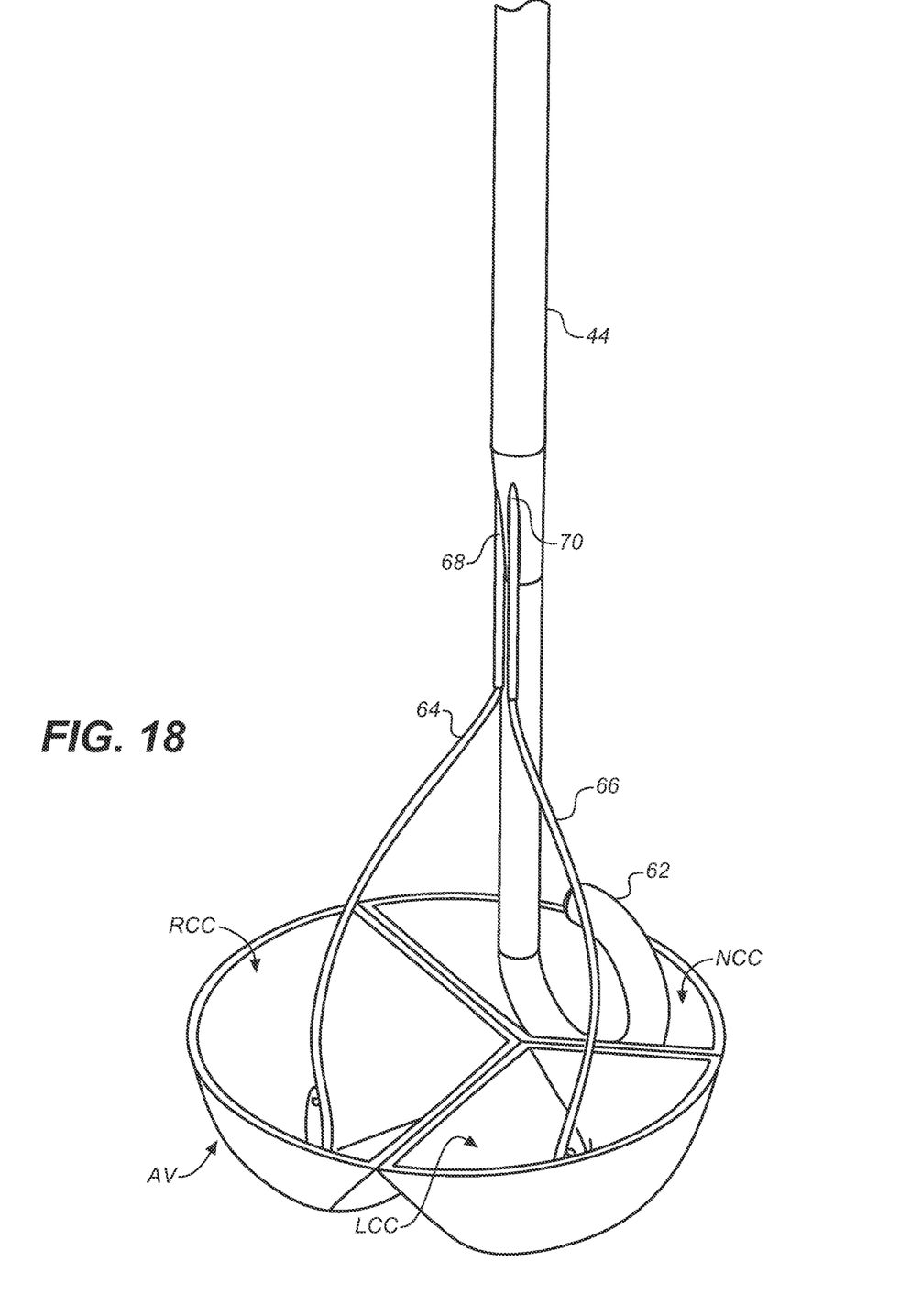
FIG. 18 is a detailed upper perspective view of the pigtail catheter and pre-shaped wires disposed, one each respectively, in the three cusps of a schematically illustrated aortic valve.
Figure 19:
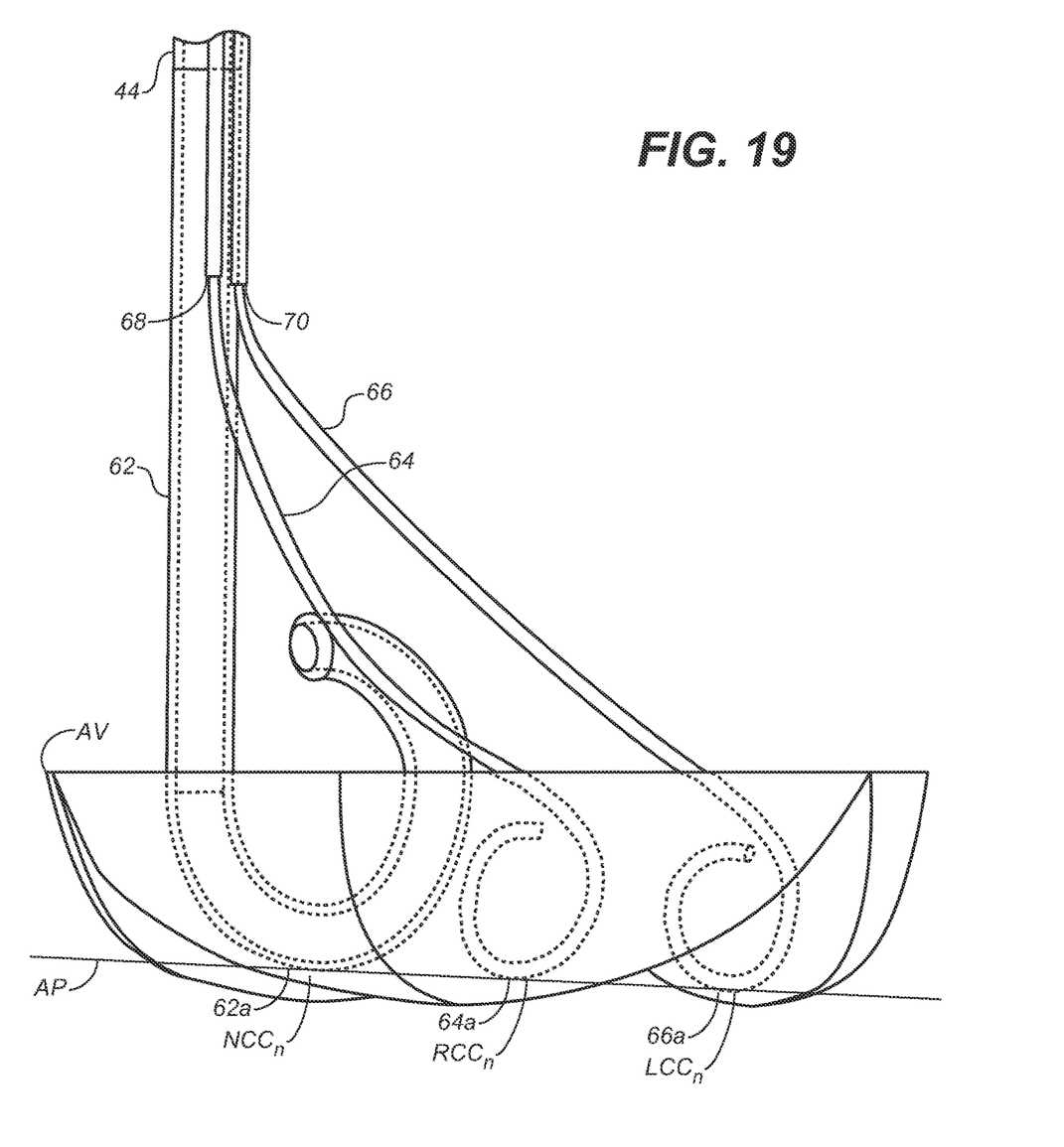
FIG. 19 is a detailed perspective view showing the distal ends of the pigtail catheter and the pre-shaped wires disposed in the cusps of a schematically depicted aortic valve defining the virtual annulus plane.

Looking at FIGS. 18-19, there is shown a method of using the inventive device (multilumen) to define the annulus plane. Method steps include the insertion of the annulus plane catheter into an access introducer sheath and advancing the catheter tip to the valve annulus under fluoroscopic guidance. Advancement of the pre-shaped wire distal sections into the individual cusps is performed and verified under fluoroscopy. First the pigtail catheter, and then each of the pre-shaped wires independently, is extended and then rotated until the nadir of each approximates the nadir of each of the cusps. The fluoroscope C-arm is then rotated until the nadir of each of the pre-shaped wires defines a plane, and the C-arm settings (angles) are noted. The annulus plane has thus been defined.

Positioning of the annulus plane catheter in a schematic aortic valve can be seen in FIG. 18, which shows details of the pigtail catheter 62 and pre-shaped wires 64, 66 disposed, one each respectively, in the right coronary cusp RCC, non-coronary cusp NCC, and left coronary cusp LCC, respectively, of the aortic valve AV. FIG. 19 shows the distal ends (apices) of the pigtail catheter 62a and the pre-shaped wires, 64a, 66a, engaging the cusps at or very close to the hinge points, or basal attachments of the valve leaflets, or most distal portion of cusps, RCCn, NCCn, and LCCn, respectively, and thereby providing connection points with which to construct and locate a virtual annulus plane AP under fluoroscopy.

Looking next at FIGS. 20-23, there is shown an alternative coaxial multi-lumen catheter configuration 200. In this iteration, the coaxial multilumen catheter includes a first pigtail catheter 202 having a primary shaft 202a, a distal primary curve 202b, a secondary curve 202c, and a proximal end 202d. The first pigtail catheter has an interior diameter sufficient to accommodate slidable insertion of a second pigtail catheter 204, having a shaft 204a, a primary curve 204b, a secondary curve 204c, and a proximal end 204d, which extends beyond the proximal end 202d of the primary shaft 202a of the first pigtail catheter 202. The second pigtail catheter is selectively extended from and retracted into a pigtail side port 206 in the secondary curve 202c of the first pigtail catheter for deployment at a cardiac valve. The second pigtail catheter is, in turn, axially and slidably disposed over and around a guide wire 208, which is selectively extended from and retracted into a guide wire side port 210 in the proximal portion of the secondary curve 204c of the second pigtail catheter. The guide wire includes a proximal end 208a which extends beyond the proximal end 204d of the second pigtail catheter.

In using the inventive device (coaxial lumens) to define the annulus plane, method steps include the insertion of the annulus plane catheter into an access introducer sheath and advancing the catheter tip to the valve annulus under fluoroscopic guidance. With the catheter tip near the annulus, the guidewire is retracted allowing the first pre-shaped pigtail catheter to form and be manipulated into the right coronary cusp RCC. Advancement of the second pigtail catheter is achieved through the side-port of the first catheter and manipulated accordingly into the left coronary cusp LCC. To complete the definition of the annulus plane, the guidewire is advanced through the side-port of the second catheter and manipulated into the non-coronary cusp NCC. [Noted: The multilumen catheter shown in FIGS. 20-22 may be configured to enable pigtail insertion into a coronary cusp in any procedural order.] Advancement of the pigtail catheter distal sections into the individual cusps is performed and verified under fluoroscopy. The fluoroscope C-arm is then rotated until the nadir of each of the pre-shaped catheters and guidewire defines a plane, and the C-arm settings (angles) are noted. The annulus plane has thus been defined.

It should be noted that the pre-shaped wires are each curved in two directions, including a first gentle curvature in a first direction, and a second curvature into the loop, wherein the loop and the direction of the first curvature lie in the same geometric plane. Accordingly, when extending the pre-shaped wires from the distal exit port, back and forth (lateral) movement of the wire in the plane of the loop can be effected by retracting and extending (respectively) the wire into and from the exit port. Combined with the radial movement effected by imparting a torque to the wire using the controls on the catheter handle, a user is able to sweep a broad region within the valve cusp to find and define the respective leaflet nadirs. The pre-shaped wires may include curvature in directions other than those listed previously to prevent interaction with other procedural elements or devices as needed. It should also be noted that this functionality also applies to the coaxial lumen catheter in that the pigtail catheters that engage into each cusp may be shaped either in a single plane curvature or each curved in multiple directions as previously described.

Figure 20:
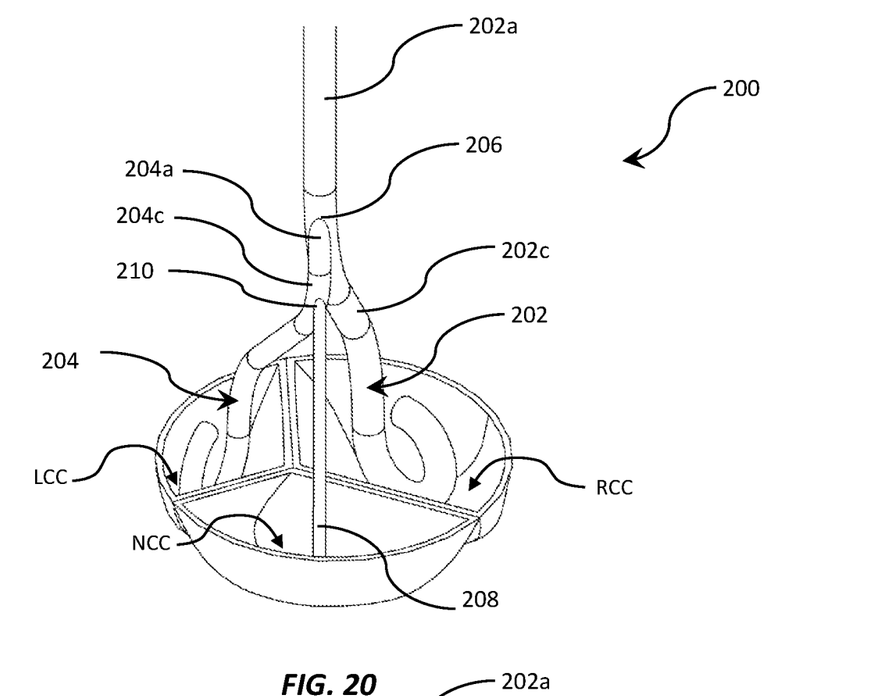
FIG. 20 is a detailed upper perspective view of an alternative embodiment of a multiple coaxial lumen catheter with reversed pigtail curvature and pre-shaped guidewire disposed, one each respectively, in the three cusps of a schematically illustrated aortic valve.
Figure 21:
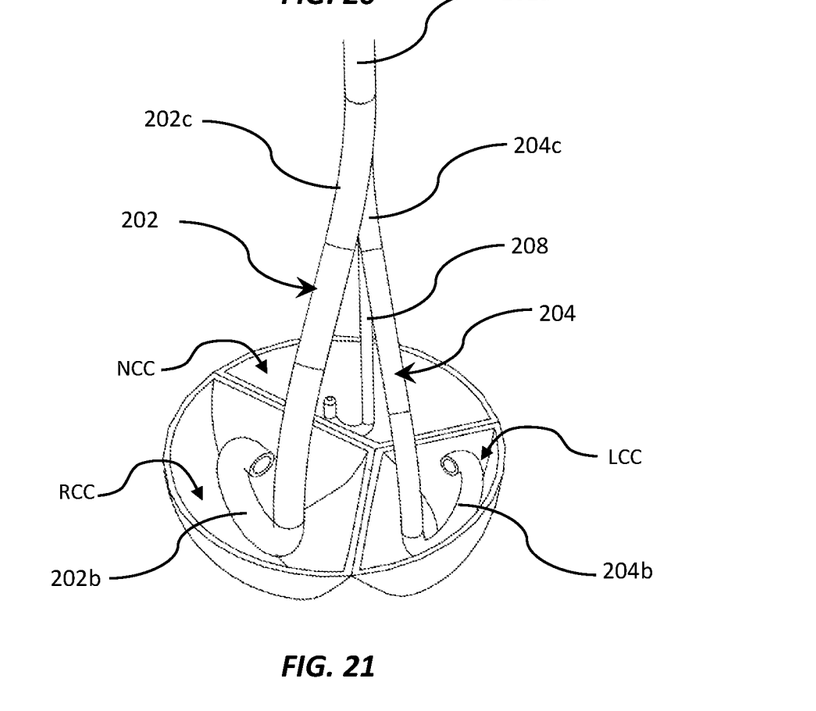
FIG. 21 is an opposing detailed upper perspective view of the multiple coaxial lumen catheter with reversed curvature pigtails and pre-shaped guidewire disposed, again showing one each respectively, in the three cusps of a schematically illustrated aortic valve.

FIG. 20, shows positioning of the annulus plane catheter (schematically shown here deployed in the aortic valve), wherein the guidewire 208 and first and second pigtail catheters 202, 204 are disposed, one each respectively, in the non-coronary cusp NCC, the right coronary cusp RCC, and the left coronary cusp LCC, respectively, of the aortic valve AV. [Note: Reference to the aortic valve is non-limiting and for illustrative purposes only. The inventive device is suitable for use in determining the annulus plane of all cardiac valves.] The first and second catheter side-ports are shown in FIG. 21 as 206 and 210, respectively. FIG. 21 is an opposing view of the annulus catheter engaging the cusps.

Figure 22:
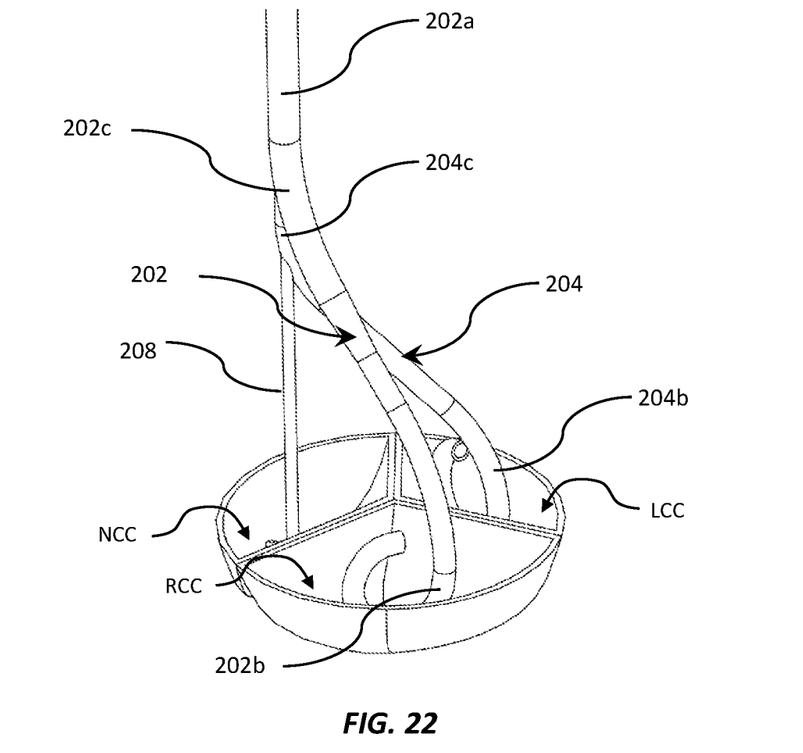
FIG. 22 is a detailed upper perspective view thereof.

FIG. 22 shows a variation of the reduced diameter pigtail catheter 204 engaged in the right coronary cusp RCC.

Figure 23:
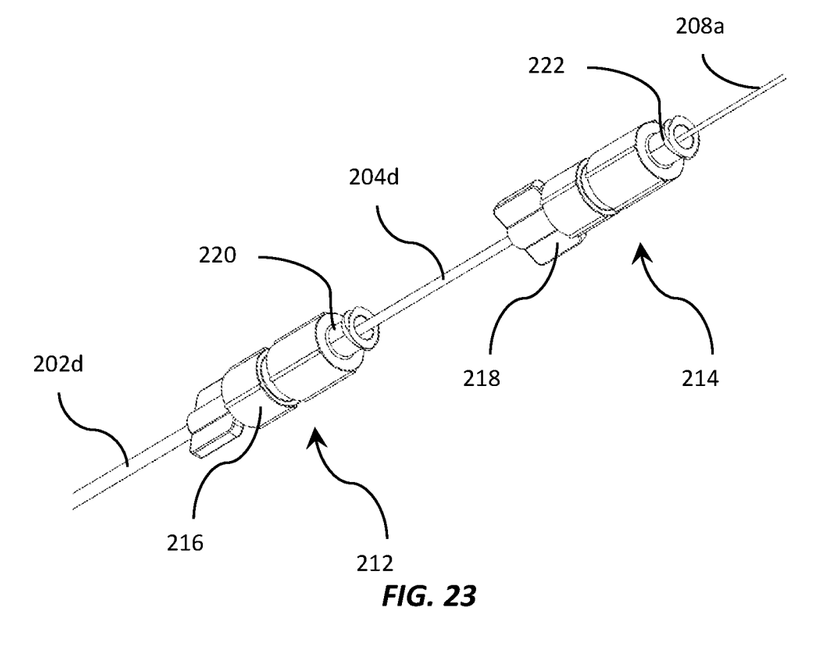
FIG. 23 is a side view of the multiple coaxial annulus catheter controls grips with separate individually controlled lumens utilizing hemostasis valves and flush ports.

FIG. 23 illustrates the coaxial lumen catheter control assembly in its simplest form, adapted for use with the two-pigtail embodiment. The pigtail catheters 202, 204 and guidewire 208 are shown in an isometric view with first and second control fittings 212, 214, including first and second hemostasis valves 216, 218 for the first and second pigtail catheters, respectively, and first and second flush ports 220 and 222, also for the first and second pigtail catheters. A handle as previously described may be incorporated with the coaxial lumen catheter as well, though a handle is obviated by this configuration. Indeed, independent control of each catheter is facilitated and simplified, enabling a surgeon to freely manipulate each entirely independently of one another, both as to depth (relative lengths) and rotationally (they can be moved in opposing directions entirely independently), and thereby to more easily determine the valve annulus using fluoroscopy in connection with radiopaque markers on the catheter tips.

The advancement of the replacement valve delivery system may occur after determining the C-arm position for an orthogonal view of the annulus plane. The pre-shaped wires (or the pigtails in an alternative configuration, as discussed with respect to FIGS. 20-23) can then be withdrawn into the annulus plane catheter tip at any time to avoid interference with another device and later redeployed as needed.

The annulus plane catheter is fabricated from materials commonly found in medical devices, including, among others, extrusions, shape memory wires, radiopaque materials, injection molded, and machined components. The inventive annulus plane catheter is compatible with standard-sized catheter sheaths and guidewires. The views show the outer tubular member with break lines indicating that it is not shown in its entirety. The characteristics of the structure are established on each side of the break lines, and the actual relative length is variable and tailored to the access point specific to the particular catheterization procedure.

It should be noted, moreover, that it may be disadvantageous to make the catheter shaft outer diameter greater than 10 F, as most pigtail angiographic catheters are compatible with 5-7F introducer sheaths. A smaller diameter is generally preferred for controlling hemostasis and promoting healing at vascular access sites.

The above disclosure is sufficient to enable one of ordinary skill in the art to practice the invention, and provides the best mode of practicing the invention presently contemplated by the inventor. While there is provided herein a full and complete disclosure of the preferred embodiments of this invention, it is not desired to limit the invention to the exact construction, dimensional relationships, and operation shown and described. Various modifications, alternative constructions, changes and equivalents will readily occur to those skilled in the art and may be employed, as suitable, without departing from the true spirit and scope of the invention. Such changes might involve alternative materials, components, structural arrangements, sizes, shapes, forms, functions, operational features or the like.

Therefore, the above description and illustrations should not be construed as limiting the scope of the invention, which is defined by the appended claims.

What is claimed as invention is:

1. An annulus plane catheter, comprising:
   a multilumen catheter having a proximal end and a distal end, said multi-lumen catheter having radiopaque markers and curvatures and sized to enclose at least two shaped wire lumens, said multilumen catheter having two distal wire ports proximate said distal end;
   first and second shaped wire lumens disposed in said multilumen catheter, each of said shaped wired lumens having a proximal end with a shaped wire insertion port and an open distal end at one of said distal wire ports;
   a pigtail catheter connected to said distal end of said multilumen catheter;
   two radiopaque shaped wires, one each slidingly disposed in one of said shaped wire lumens, each of said shaped wires having a proximal end and a distal end and sized to fit into a range of annulus diameters and/or depths; and
   a catheter delivery handle including a housing defining a substantially hollow interior space and having a proximal end and a distal end, said distal end capturing and enclosing said multilumen catheter, and first and second longitudinal slots disposed in said housing;
   first and second thumb/finger-actuated sliders operatively coupled to respective first and second shaped wires and slidingly disposed in a respective one of said first and second longitudinal slots to enable extension and retraction of said shaped wires through said lumens;
   wherein said longitudinal slots in said handle have a width sufficient to enable side-to-side motion of said sliders, thereby enabling a torque to be imparted to and translated down said first and second shaped wires to said distal end of said first and second shaped wires, such that said distal end of each of said shaped wires may be individually controlled and rotated to address differing annulus diameters.

2. The annulus plane catheter of claim 1, wherein said multilumen wire and each of said first and second shaped wires include visual markers.

3. The annulus plane catheter of claim 1, wherein said handle further includes homeostasis controls and at least one flush port.

4. An annulus plane catheter, comprising:
   a handle defining a hollow interior;
   a multilumen catheter operatively coupled to said handle and having an outer tubular member with a proximal portion captured in said housing, and a distal end portion, said distal end portion including a plurality of distal wire ports through which shaped wires may extend and retract;
   a pigtail catheter connected to and extending from said distal end portion;
   a plurality of shaped wire lumens axially disposed in said multilumen catheter, each including a shaped wire slidably disposed therein, said shaped wires having a proximal end and a curved distal end when extended from its respective lumen; and
   fingertip controls disposed on said handle, one each operatively connected to each of said shaped wires to extend and retract said shaped wires to and from said distal wire ports.

5. The annulus plane catheter of claim 4, wherein said pigtail catheter includes one or more side ports though which to promote contrast media distribution.

6. The annulus plane catheter of claim 4, wherein said fingertip controls each include a slider slidably disposed in a longitudinal slot in said housing, each of said fingertip controls connected to a sliding rod slidingly disposed in said housing, and each sliding rod coupled to a proximal end of one of said shaped wires.

7. The annulus plane catheter of claim 6, wherein said outer tubular member of said multilumen catheter is centered in said housing.

8. The annulus plane catheter of claim 6, wherein said fingertip controls include flat buttons shaped with curvature to conform to the shape of said housing and including surface features to enhance slip-free finger engagement.

9. The annulus plane catheter of claim 6, wherein said longitudinal slots are parallel longitudinal slots.

10. The annulus plane catheter of claim 9, wherein said longitudinal slots are sized to allow approximately 10-25 degrees of lateral motion of said fingertip control, thereby imparting approximately 10-25 degrees of rotational motion of said curved distal ends of said shaped wires.

11. The annulus plane catheter of claim 4, wherein each of said shaped wires inserts into a wire fitting disposed in said housing and having a proximal end insertion point.

12. The annulus plane catheter of claim 11, wherein said proximal end insertion points each include a fluid seal.

13. The annulus plane catheter of claim 4, further including flush ports in fluid communication with said multilumen catheter to enable the introduction of solutions to prevent catheter occlusion and clot formation.

14. The annulus plane catheter of claim 4, wherein said distal end of said handle includes a strain relief through which said tubular member passes.

\* \* \* \* \*